United States Patent [19]

Aso et al.

[11] Patent Number: 5,564,427
[45] Date of Patent: Oct. 15, 1996

[54] BLOOD PRESSURE MONITORING SYSTEM

[75] Inventors: Shigeru Aso; Hiroshi Sakata; Yoshihiro Sugo; Hidehiro Hosaka, all of Tokyo, Japan

[73] Assignee: Nihon Kohden Corporation, Tokyo, Japan

[21] Appl. No.: 413,850

[22] Filed: Mar. 30, 1995

[30] Foreign Application Priority Data

Mar. 30, 1994 [JP] Japan .................................... 6-061409
Mar. 16, 1995 [JP] Japan .................................... 7-056940

[51] Int. Cl.$^6$ ........................................... A61B 5/00
[52] U.S. Cl. ............................ 128/681; 128/682; 128/687
[58] Field of Search ......................... 128/677, 680–683, 128/687

[56] References Cited

U.S. PATENT DOCUMENTS 4,907,596  3/1990  Schmid et al. ........................ 128/687
5,237,997  8/1993  Greubel et al. ....................... 128/672
5,279,303  1/1994  Kawamura et al. ................... 128/687

*Primary Examiner*—Angela D. Sykes
*Assistant Examiner*—Robert L. Nasser, Jr.
*Attorney, Agent, or Firm*—Sughrue, Mion, Zinn, Macpeak & Seas

[57] ABSTRACT

A blood pressure monitoring system includes a blood pressure measurement device for measuring blood pressure using a cuff, a memory for storing an externally inputted pulse wave propagation time fluctuation threshold, a time interval detection reference point detection section for detecting a time interval detection reference point in a pulse wave on the side of aortae of a living organism, a pulse wave detection section for detecting a pulse wave on the side of peripheral blood vessels appearing with a time lag with respect to the pulse wave on the side of aortae, a pulse wave propagation time measurement section for measuring a pulse wave propagation time based on respective detected outputs from the time interval detection reference point detection section and the pulse wave detection section, an operation device for calculating a pulse wave propagation fluctuation from two measured pulse wave propagation times, a judgment device for judging whether or not the calculated pulse wave propagation time fluctuation exceeds the pulse wave propagation time fluctuation threshold read from the memory, and a control device for controlling the blood pressure measurement device based on an output of the judgment device so that the blood pressure of a subject is measured using the cuff.

4 Claims, 4 Drawing Sheets

BLOOD PRESSURE MONITORING SYSTEM

BACKGROUND OF THE INVENTION

1. Field of the Invention

The invention relates to a blood pressure monitoring system in fields requiring continuous blood pressure monitoring of a patient in an operating room, an intensive care unit, a first-aid room, an extracorporeal dialysis room, and the like. More particularly, the invention is directed to a blood pressure monitoring system utilizing pulse wave propagation time.

2. Related Art

To monitor the blood pressure of a subject by continuously measuring his or her blood pressure, the following methods have heretofore been available. An oscillometric, noninvasive method is designed to measure blood pressure by wrapping a cuff to the upper part of an arm of the subject. A direct, invasive method is designed to measure blood pressure by puncturing an artery of the subject.

By the way, the noninvasive blood pressure measuring method using the cuff may, in some cases, overlook a drastic change in blood pressure due to a shock when the measuring cycle in fixed time measurement is long (e.g., when the measuring cycle is set to 5 minutes or more).

If the measuring cycle is reduced to, e.g., 1 minute to overcome this problem, the blood vessel around which the cuff is wrapped is burdened, which in turn imposes the problem of causing internal hemorrhage.

Further, in the case of fixed time measurement, frequently applied cuff wrapping force that is more than necessary burdens the patient, and therefore causes somnipathy and the like.

On the other hand, the direct, invasive blood pressure measurement not only gives the subject a mental burden due to invasion or brings about the problem of infection, but also gives too much work to the medical staff by involving more labor than in noninvasive blood pressure measurement.

SUMMARY OF THE INVENTION

The invention has been proposed to overcome these problems encountered by the conventional art. Accordingly, the object of the invention is to provide a blood pressure monitoring system capable of monitoring the blood pressure of a subject continuously in safety without burdening the subject.

A blood pressure monitoring system based on the aforementioned measurement principle of the invention includes: a blood pressure measurement means for measuring blood pressure using a cuff; a memory for storing an externally inputted pulse wave propagation time fluctuation threshold; a time interval detection reference point detection means for detecting a time interval detection reference point in a pulse wave on the side of aortae of a living organism; a pulse wave detection means for detecting a pulse wave on the side of peripheral blood vessels appearing with a time lag with respect to the pulse wave on the side of aortae; a pulse wave propagation time measurement section for measuring a pulse wave propagation time based on respective detected outputs from the time interval detection reference point detection means and the pulse wave detection means; an operation means for calculating a pulse wave propagation fluctuation from two measured pulse wave propagation times; a judgment means for judging whether or not the calculated pulse wave propagation time fluctuation exceeds the pulse wave propagation time fluctuation threshold read from the memory; and a control means for controlling the blood pressure measurement means based on an output of the judgment means so that the blood pressure of a subject is measured using the cuff.

Further, a blood pressure monitoring system of the invention includes: a blood pressure measurement means for measuring blood pressure using a cuff; a memory for storing a pulse wave propagation time fluctuation threshold and a blood pressure fluctuation threshold, the thresholds being inputted from an external means; a time interval detection reference point detection means for detecting a time interval detection reference point in a pulse wave on the side of aortae of a living organism; a pulse wave detection means for detecting a pulse wave on the side of peripheral blood vessels appearing with a time lag with respect to the pulse wave on the side of aortae; a pulse wave propagation time measurement section for measuring a pulse wave propagation time based on respective detected outputs from the time interval detection reference point detection means and the pulse wave detection means; a first operation means for calculating a pulse wave propagation time fluctuation from two measured pulse wave propagation times; a second operation means for calculating constants inherent in a subject by dividing a difference between two blood pressure values obtained by the blood pressure measurement means by a difference between the two measured pulse wave propagation times; a third operation means for updating the pulse wave propagation time fluctuation threshold within the memory by dividing the blood pressure fluctuation threshold read from the memory by the calculated constants inherent in the subject; a first control means for controlling the operation of updating the pulse wave propagation time fluctuation threshold; a judgment means for judging whether or not the calculated pulse wave propagation time fluctuation exceeds the pulse wave propagation time fluctuation threshold read from the memory; and a second control means for controlling the blood pressure measurement means based on an output of the judgment means so that the blood pressure of the subject is measured using the cuff.

According to the present invention, the blood pressure of a subject can be measured by measuring a pulse wave propagation time fluctuation and consecutively judging whether or not the measured pulse wave propagation time fluctuation exceeds a pulse wave propagation time fluctuation threshold. As long as the blood pressure is measured correctly using the cuff when the pulse wave propagation time fluctuation has exceeded the pulse wave propagation time fluctuation threshold, burdens given to the subject can be minimized.

Further, according to the present invention, the pulse wave propagation time fluctuation threshold is updated. Therefore, the operation of monitoring the blood pressure of the subject can be performed more accurately.

DETAILED DESCRIPTION OF THE PREFERRED EMBODIMENTS

Embodiments of the invention will now be described in detail with reference to the drawings.

The basic concept of the invention will now be described below.

A blood pressure measuring apparatus that measures blood pressure from pulse wave propagation speed (the time required for a pulse wave to be propagated a predetermined distance) is known as a noninvasive blood pressure measuring apparatus.

The principle of blood pressure measurement based on the pulse wave propagation speed can be explained in the following way.

Figure 4:
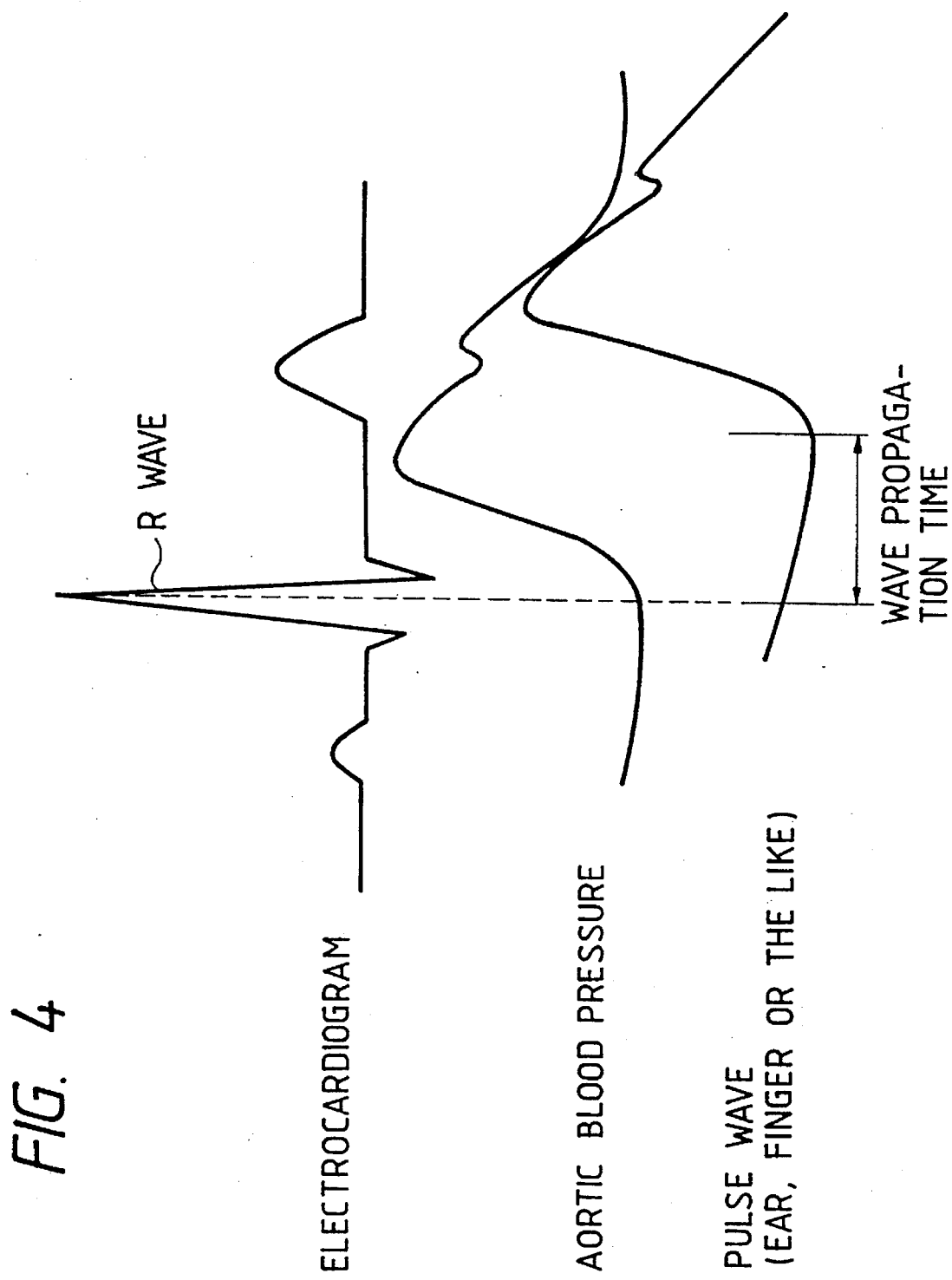
FIG. 4 is a waveform diagram illustrative of a pulse wave propagation time.

The pulse wave propagation time will be described first. As shown in FIG. 4, a specific point of a pulse wave on the side of peripheral blood vessels such as a finger or a ear appears with a time lag with respect to a specific point of an aortic pulse wave. This time lag is the pulse wave propagation time.

The pulse wave propagation speed corresponding to the time required for a pulse wave to be propagated a predetermined distance is expressed in the form of a function of the modulus of volumetric elasticity of a blood vessel. When the blood pressure increases, the modulus of volumetric elasticity of the blood vessel is increased; the blood vessel wall hardens; and the propagation speed is increased. Therefore, a blood pressure fluctuation can be found from the pulse wave propagation speed.

The blood pressure measuring apparatus based on the pulse wave propagation time measures blood pressure by using a cuff or the like and must make a calibration with reference to the measured blood pressure data.

For the calibration, blood pressures and pulse wave propagation times are measured when a subject is at rest and when the subject is in exercise.

Here, let it be assumed that the blood pressure and the pulse wave propagation time when the subject is at rest are P1, T1; the blood pressure and the pulse wave propagation time when the subject is in exercise are P2, T2; and constants inherent in the subject are $\alpha$, $\beta$. Then, the blood pressures P1, P2 are given as $$P1 = \alpha T1 + \beta$$

$$P2 = \alpha T2 + \beta$$

Therefore, by measuring P1, T1, P2, T2, the constants $\alpha$, $\beta$ can be calculated from the above two equations. Once the constants $\alpha$, $\beta$ have been calculated, the blood pressure of the subject can be measured only by measuring the pulse wave propagation time from then on.

To measure two different blood pressures, measurement may be made at any timings at which two different blood pressures appear; measurement may not necessarily be made when the subject is at rest and in exercise.

On the other hand, the blood pressure fluctuation of the subject could be monitored simply by measuring the pulse wave propagation time consecutively. In this case, the procedure to be taken is as follows. First, it is judged that a drastic change has occurred in the blood pressure fluctuation of the subject when a pulse wave propagation time fluctuation $\Delta T$ has exceeded a preset pulse wave propagation time fluctuation threshold $\Delta T_s$. Then, the blood pressure is noninvasively measured correctly using the cuff at such timing of drastic change.

Since this procedure frees the subject from burdens accompanied in the case where the blood pressure is measured continuously at a predetermined cycle using the cuff, the burdens borne by the subject can be remarkably alleviated.

Figure 1:
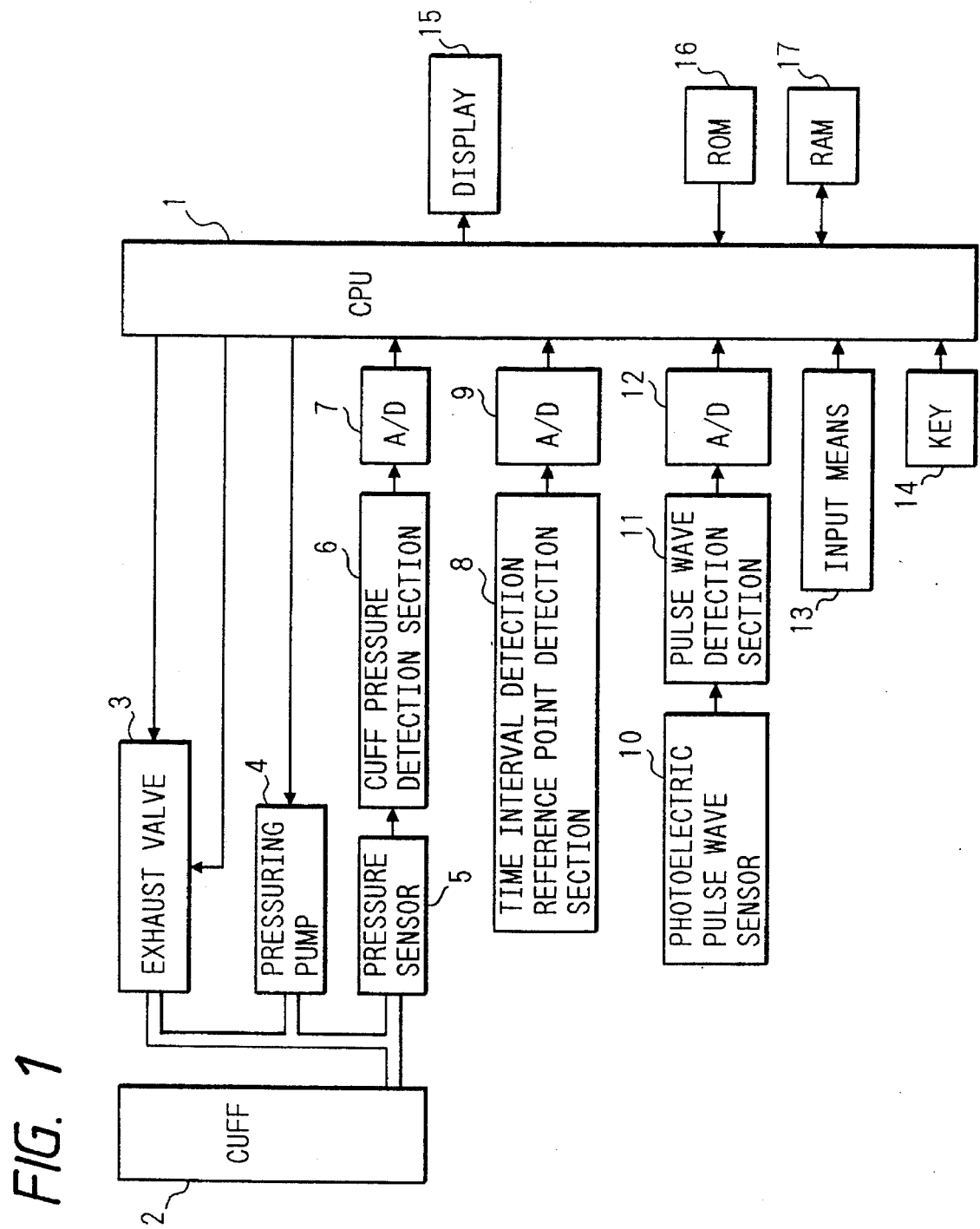
FIG. 1 is a block diagram showing a blood pressure monitoring system, which is an embodiment of the invention.

FIG. 1 shows a blood pressure monitoring system, which is an embodiment of the invention, in the form of a block diagram. In FIG. 1, a cuff 2 is designed to be put on the upper part of an arm or a finger of a subject. An exhaust valve 3 opens and closes the cuff with respect to the atmosphere. The air is supplied to the cuff 2 by a pressuring pump 4. A pressure sensor 5 is attached to the cuff main body, and a sensor output is detected by a cuff pressure detection section 6. The output of the cuff pressure detection section 6 is converted into a digital signal by an A/D converter 7, and inputted to a CPU (Central Processing Unit) 1.

A time interval detection reference point detection section 8 is designed to detect a timing at which the aortic pressure hits the bottom value substantially simultaneously with the generation of an R wave in an electrocardiogram. The output of this detection section is converted into a digital signal by an A/D converter 9, and inputted to the CPU 1. The time interval detection reference point detection section 8 may include an electrode attached to the chest of a subject, and an electrocardiographic R wave detection section to which the electrode is connected. Further, the time interval detection reference point detection section 8 may, instead, include a photoelectric pulse wave sensor or pressure pulse wave sensor for detecting the pulse wave of the aorta, and a pulse wave detection section to which either one of these sensors is connected.

On the other hand, the photoelectric pulse wave sensor 10 is attached to, e.g., a finger of a subject to measure the pulse wave on the side of peripheral blood vessels. The output of this sensor 10 is applied to the pulse wave detection section 11, so that the pulse wave at the position of the subject to which the sensor 10 is attached can be detected. The output of the pulse wave detection section 11 is inputted to the CPU 1 after converted into a digital signal by an A/D converter 12.

A key 14 is pressed either to manually measure blood pressure with the cuff 2 or to update a pulse wave propagation time fluctuation threshold $\Delta T_s$.

An initial pulse wave propagation time fluctuation threshold $\Delta T_s$ and a blood pressure fluctuation threshold $\Delta BP_s$ are inputted from an input means 13.

The CPU 1 executes a processing program based on signals inputted from the A/D converters 7, 9, 12 and the key 14 to not only output necessary signals to the exhaust valve 3, the pressuring pump 4, and the like, but also output processed results to a display 15. A memory (ROM) 16 that is connected to the CPU 1 stores the processing program, and a memory (RAM) 17 that is also connected to the CPU 1 stores in-process data.

It may be noted that the CPU 1 constitutes a pulse wave propagation time measurement section, an operation means, a judgment means, and a control means, and further constitutes first to third operation means, and first and second control means.

Figure 2:
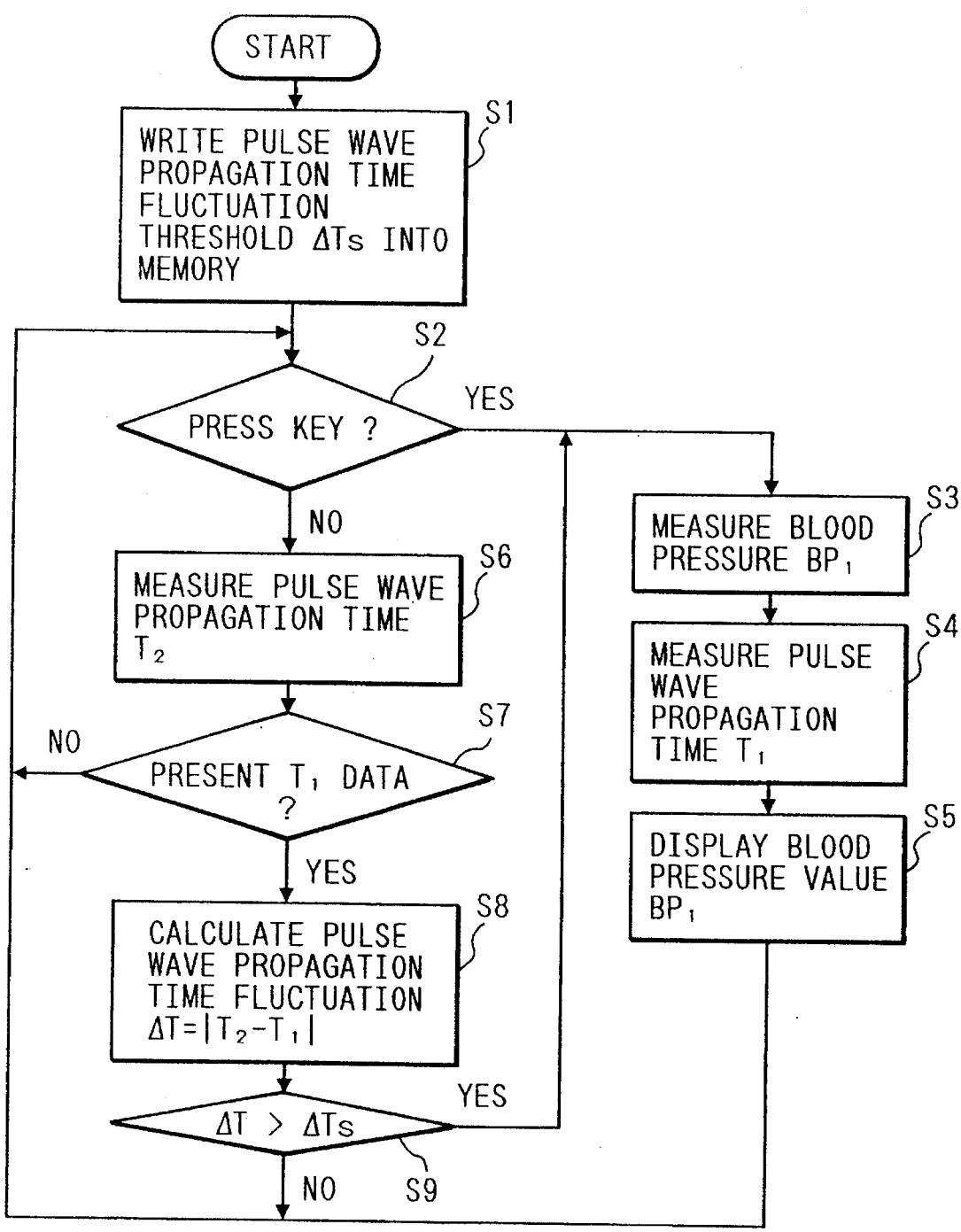
FIG. 2 is a flowchart illustrative of an operation of the blood pressure monitoring system of FIG. 1.

An operation of the thus constructed blood pressure monitoring system will be described with reference to a flowchart shown in FIG. 2.

First, the pulse wave propagation time fluctuation threshold $\Delta T_s$ is inputted from the input means 13, and written to the memory 17 in Step S1.

Then, whether or not the key 14 has been pressed is judged in Step S2. If the key has been pressed, the exhaust valve 3 and the pressuring pump 4 are controlled by the CPU 1 to start measuring the blood pressure of a subject using the cuff 2 in Step S3. At this instance, the data supplied from the A/D converter 7 is processed within the CPU 1, and a blood pressure value BP1 measured by an oscillometric method is written to the memory 17.

Then, a pulse wave propagation time T1 is measured based on the data inputted to the CPU 1 from the A/D converters 9, 12, and the measured value is written to the memory 17 in Step S4. The pulse wave propagation time T1 is equivalent to a time from a timing at which the aortic pressure hits the bottom value substantially simultaneously with the generation of an R wave in an electrocardiogram to a timing at which the pulse wave hits the bottom value on the side of peripheral blood vessels.

Subsequently, the previously measured blood pressure value BP1 is displayed on the display 15 in Step S5. The system then returns to Step S2.

In Step S2, whether or not the key has been pressed is judged again. If the key has not been pressed, a pulse wave propagation time $T_2$ is measured based on the data from the A/D converters 9, 12, and the measured value is written to the memory 17 in Step S6.

Then, in Step S7, whether or not the previously measured pulse wave propagation time T1 data is present is judged. If the data is present, a pulse wave propagation time fluctuation $\Delta T$ is calculated based on the following equation using T1, T2 in Step S8.

$$\Delta T = |T2-T1|$$

Then, in Step S9, whether or not the pulse wave propagation time fluctuation $\Delta T$ calculated in Step S8 exceeds the pulse wave propagation time fluctuation threshold $\Delta T_s$ inputted in advance is judged; i.e., whether or not $\Delta T$ satisfies an inequality $\Delta T > \Delta T_s$ is judged. If $\Delta T > \Delta T_s$ is not satisfied, the system returns to Step S2 to repeat a series of processing.

On the other hand, if it is judged that $\Delta T > \Delta T_s$ is satisfied in Step S9, the system deems that a drastic change such as a shock has occurred in the blood pressure fluctuation of the subject, and therefore proceeds to Step S3.

In Step S3, to handle the drastic change in the blood pressure fluctuation of the subject, blood pressure is measured with the cuff 2, and the measured value BP1 is written to the memory 17.

Successively, the pulse wave propagation time T1 is measured based on the data from the A/D converters 9, 12 again, and the measured value is written to the memory 17 in Step S4.

In Step S5, the blood pressure measured in Step S3 is displayed on the display 15. The system then returns to Step S2.

By judging whether or not the pulse wave propagation time fluctuation $\Delta T$ exceeds the pulse wave propagation time fluctuation threshold $\Delta T_s$ while measuring the pulse wave propagation time at all times in this way, a drastic change in the blood pressure fluctuation of a subject is monitored. In addition, blood pressure is measured correctly using the cuff 2 when a drastic change in the blood pressure fluctuation has been monitored. Therefore, the burden conventionally given to the subject can be reduced significantly.

Figure 3:
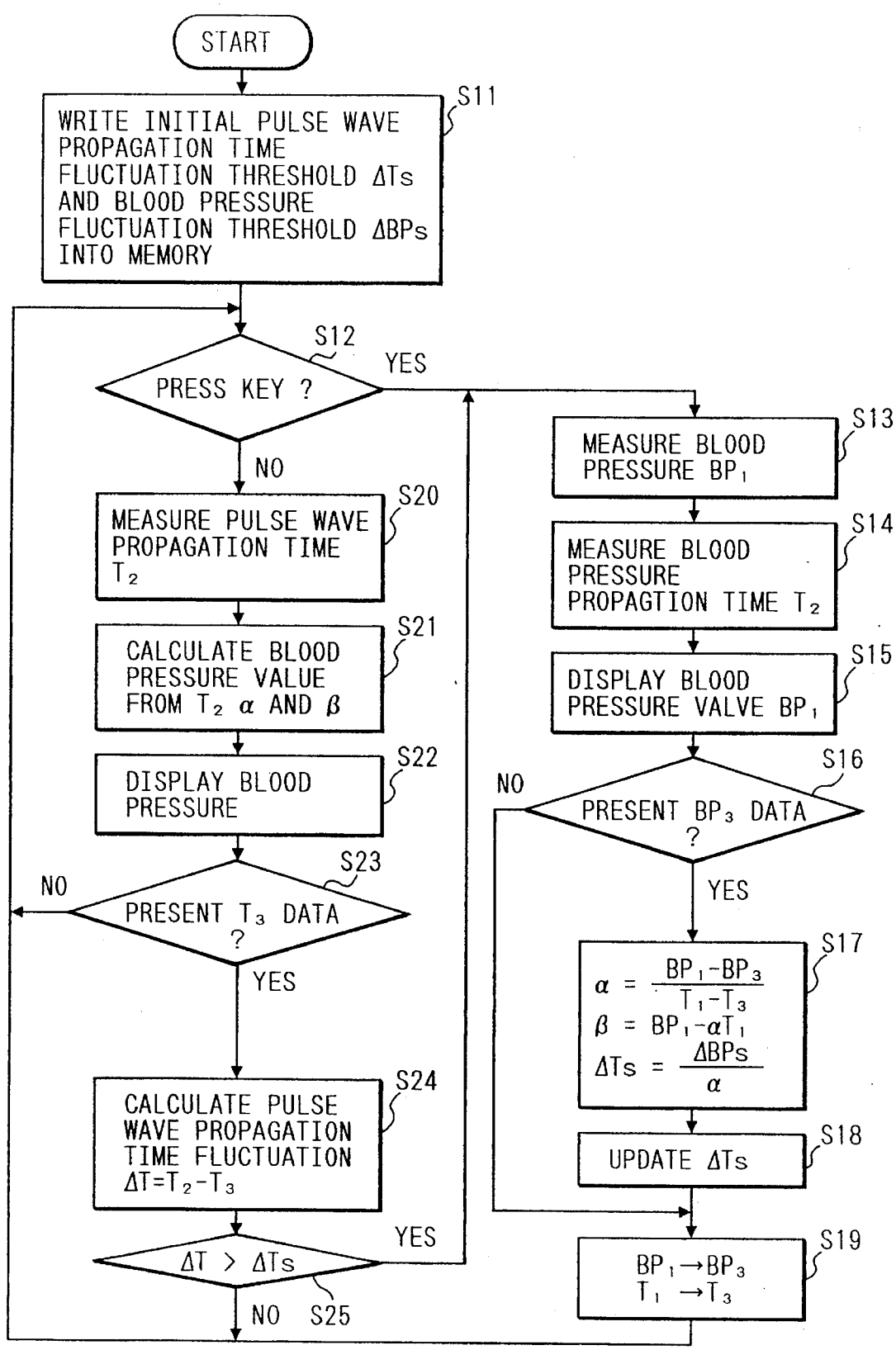
FIG. 3 is a flowchart illustrative of an operation of another embodiment of the invention.

An operation of another embodiment in the case of correcting the pulse wave propagation time fluctuation threshold $\Delta T_S$, will be described next with reference to a flowchart shown in FIG. 3.

First, the initial pulse wave propagation time fluctuation threshold $\Delta T_s$ and a blood pressure fluctuation threshold $\Delta BP_s$, are inputted from the input means 13, and written to the memory 17 in Step S11.

Then, whether or not the key 14 has been pressed is judged in Step S12. If the key has been pressed, blood pressure is made with the cuff 2, and the measured value BP1 is written to the memory 17 in Step S13.

Then, the pulse wave propagation time T1 is measured based on the data from the A/D converters 9, 12, and written to the memory 17 in Step S14.

Then, the previously measured blood pressure value BP1 is displayed on the display 15 in Step S15.

Successively, whether or not measured blood pressure value data BP3 is present is judged in Step S16. If the data is not present, not only the blood pressure value BP1 is written to the memory 17 as BP3, but also the pulse wave propagation time T1 is written to the memory 17 as T3 in Step S19. The system then returns to Step S12.

If it is judged that the measured blood pressure value data BP3 is present in Step S16, values $\alpha$, $\beta$, and $\Delta T_s$ are calculated based on the following equations.

$$\alpha = (BP1-BP3)/(T1-T3)$$

$$\beta = BP1 - \alpha T1$$

$$\Delta T_s = \Delta BP_s / \alpha$$

The calculated constants $\alpha$, $\beta$ inherent in a subject are written to the memory 17, and used thereafter to calculate a blood pressure using the pulse wave propagation time T2.

Further, the pulse wave propagation time fluctuation threshold $\Delta T_s$ is updated to the calculated value, and written to the memory 17 in Step S18.

Successively, not only the blood pressure value BP1 is written to the memory 17 as BP3, but also the pulse wave propagation time T1 is written to the memory 17 as T3 in Step S19. The system then returns to Step S12.

In Step S12, whether or not the key has been pressed is judged again. If the key has not been pressed, the pulse wave propagation time T2 is measured based on the data from the A/D converters 9, 12, and the measured value is written to the memory 17 in Step S20.

Then, in Step S21, a blood pressure value P is calculated from the following equation using both the measured pulse wave propagation time T2 and the constants $\alpha$, $\beta$ calculated in Step S17, and the calculated value is written to the memory 17.

$$P = \alpha T2 + \beta$$

In Step S22, the calculated blood pressure value P is displayed on the display 15.

Successively, in Step S23, whether or not the previously measured pulse wave propagation time data T3 is present is judged. If the data is present, a pulse wave propagation time fluctuation $\Delta T$ is calculated from the following equation using T2, T3 in Step S24.

$$\Delta T = T2 - T3$$

Then, in Step S25, whether or not the pulse wave propagation time fluctuation $\Delta T$ calculated in Step S24 exceeds the pulse wave propagation time fluctuation threshold $\Delta T_s$ inputted in advance is judged; i.e., whether or not $\Delta T$ satisfies an inequality $\Delta T > \Delta T_s$ is judged. If $\Delta T > \Delta T_s$ is not satisfied, the system returns to Step S12 to repeat a series of processing.

On the other hand, if it is judged that $\Delta T > \Delta T_s$ is satisfied in Step S25, the system deems that a drastic change such as a shock has occurred in the blood pressure fluctuation of the subject, and therefore proceeds to Step S13.

In Step S13, to handle the drastic change in the blood pressure fluctuation of the subject, blood pressure is measured using the cuff 2, and the measured value BP1 is written to the memory 17.

Successively, the pulse wave propagation time T1 is measured based on the data from the A/D converters 9, 12 again, and the measured value is written to the memory 17 in Step S14.

In Step S15, the blood pressure correctly measured in Step S13 is displayed on the display 15. The system then moves to Step S16 to repeat similar processing.

As described above, this embodiment is characterized as allowing a drastic change in the blood pressure fluctuation of a subject to be monitored more correctly by updating the pulse wave propagation time fluctuation threshold $\Delta T_s$.

Moreover, a pulse wave propagation time measurement is made on a single pulse basis, or such measurements may be made at a predetermined time interval or predetermined number of pulses and the measured values may thereafter be averaged. The averaging operation contributes to more accurate measurement free from irregularly generated noise.

As described in the foregoing, the present invention is provided as not only judging whether or not a drastic change in the blood pressure fluctuation of a subject has occurred by judging whether or not the pulse wave propagation time fluctuation has exceeded the pulse wave propagation time fluctuation threshold while consecutively measuring the pulse wave propagation time, but also correctly measuring the blood pressure of the subject using a cuff when the blood pressure changes drastically. Therefore, pains such as those to which the subject is exposed when the blood pressure is measured using the cuff at a short interval or in the case of the direct, invasive blood pressure measurement in the conventional blood pressure measurement are not accompanied, so that the burden to be borne by the subject can be reduced significantly.

Further, the present invention is provided as updating the pulse wave propagation time fluctuation threshold. Therefore, the invention can provide the advantage that a drastic change in the blood pressure fluctuation of a subject can be monitored more correctly.

What is claimed is:

1. A blood pressure monitoring system comprising:

blood pressure measurement means for measuring blood pressure using a cuff;

a memory for storing an externally inputted pulse wave propagation time fluctuation threshold;

time interval detection reference point detection means for detecting a time interval detection reference point in an aortic pulse wave of a subject;

pulse wave detection means for detecting a pulse wave in peripheral blood vessels appearing with a time lag with respect to the aortic pulse wave;

pulse wave propagation time measurement section for measuring a pulse wave propagation time based on respective detected outputs from the time interval detection reference point detection means and the pulse wave detection means;

first operation means for calculating a pulse wave propagation fluctuation from two measured pulse wave propagation times;

judgment means for judging whether or not the calculated pulse wave propagation time fluctuation exceeds the pulse wave propagation time fluctuation threshold read from the memory; and control means for controlling the blood pressure measurement means based on an output of the judgment means so that the blood pressure of a subject is measured using the cuff.

2. The blood pressure monitoring system according to the claim 1, wherein the memory stores a blood pressure fluctuation threshold, and further comprising:

second operation means for calculating constants inherent in the subject by dividing a difference between two blood pressure values obtained by the blood pressure measurement means by a difference between the two measured pulse wave propagation times;

third operation means for updating the pulse wave propagation time fluctuation threshold within the memory by dividing the blood pressure fluctuation threshold read from the memory by the at least on of said calculated constants inherent in the subject; and auxiliary control means for controlling the operation of updating the pulse wave propagation time fluctuation threshold.

3. A blood pressure monitoring method comprising the steps of:

measuring blood pressure using a cuff;

storing an externally inputted pulse wave propagation time fluctuation threshold in a memory;

detecting a time interval detection reference point in an aortic pulse wave of aortae of a living organism;

detecting a pulse wave in peripheral blood vessels appearing with a time lag with respect to the aortic pulse wave;

measuring a pulse wave propagation time based on respective detected outputs from the time interval detection reference point detection means and the pulse wave detection means;

calculating a pulse wave propagation fluctuation from two measured pulse wave propagation times;

judging whether or not the calculated pulse wave propagation time fluctuation exceeds the pulse wave propagation time fluctuation threshold read from the memory; and controlling the blood pressure measurement means based on an output of the judgment means so that the blood pressure of a subject is measured using the cuff.

4. A blood pressure monitoring method comprising the steps of:

measuring blood pressure using a cuff;

storing a pulse wave propagation time fluctuation threshold and a blood pressure fluctuation threshold in a memory, the thresholds being inputted from an external means;

detecting a time interval detection reference point in an aortic pulse wave of a living organism;

detecting a pulse wave in peripheral blood vessels appearing with a time lag with respect to the aortic pulse wave;

measuring a pulse wave propagation time based on respective detected outputs from the time interval detection reference point detection means and the pulse wave detection means;

calculating a pulse wave propagation time fluctuation from two measured pulse wave propagation times;

calculating constants inherent in said living organism by dividing a difference between two blood pressure values obtained by the blood pressure measurement means by a difference between the two measured pulse wave propagation times;

updating the pulse wave propagation time fluctuation threshold within the memory by dividing the blood pressure fluctuation threshold read from the memory by the at least on of said calculated constants inherent in the subject;

controlling the operation of updating the pulse wave propagation time fluctuation threshold;

judging whether or not the calculated pulse wave propagation time fluctuation exceeds the pulse wave propagation time fluctuation threshold read from the memory; and controlling the blood pressure measurement means based on an output of the judgment means so that the blood pressure of the subject is measured using the cuff.

* * * * *